United States Patent [19]

Scheuing

[11] Patent Number: 5,465,714
[45] Date of Patent: Nov. 14, 1995

[54] ELECTRO-OPTICAL SENSOR FOR SPECTROPHOTOMETRIC MEDICAL DEVICES

[75] Inventor: Richard S. Scheuing, Ann Arbor, Mich.

[73] Assignee: Somanetics Corporation, Troy, Mich.

[21] Appl. No.: 273,366

[22] Filed: Jul. 11, 1994

Related U.S. Application Data

[63] Continuation of Ser. No. 65,140, May 20, 1993, abandoned.

[51] Int. Cl.$^6$ .................................................. A61B 5/00
[52] U.S. Cl. ............................................. 128/633; 128/666
[58] Field of Search ........................... 128/633.4, 664.7; 356/39–41

[56] References Cited

U.S. PATENT DOCUMENTS

| | | | |
|---|---|---|---|
| 2,790,438 | 4/1957 | Taplin et al. | |
| 3,230,951 | 1/1966 | Teschner | 128/666 |
| 3,602,213 | 8/1971 | Howell et al. | |
| 3,769,974 | 11/1973 | Smart et al. | |
| 3,810,460 | 5/1974 | Van Nie | |
| 3,814,081 | 6/1974 | Mori | |
| 3,822,695 | 7/1974 | Takayama | |
| 3,910,701 | 10/1975 | Henderson et al. | |
| 4,013,067 | 3/1977 | Kresse et al. | |
| 4,015,595 | 4/1977 | Benjamin, Jr. | |
| 4,063,551 | 12/1977 | Sweeney | |
| 4,091,803 | 5/1978 | Pinder | |
| 4,109,643 | 8/1978 | Bond et al. | |
| 4,163,447 | 8/1979 | Orr | 128/666 |
| 4,223,680 | 9/1980 | Jobsis | 128/633 |
| 4,249,540 | 2/1981 | Koyama et al. | 128/666 |
| 4,259,963 | 4/1981 | Huch | 128/635 |
| 4,267,844 | 5/1981 | Yamanishi | 128/633 |
| 4,281,645 | 8/1981 | Jobsis | 128/633 |
| 4,321,930 | 3/1982 | Jobsis et al. | 128/633 |
| 4,332,258 | 6/1982 | Arai et al. | 128/666 |
| 4,336,809 | 6/1982 | Clark | 128/665 |
| 4,344,438 | 8/1982 | Schultz | 128/634 |
| 4,350,163 | 9/1982 | Ford, Jr. et al. | 128/633 |
| 4,380,240 | 4/1983 | Jobsis et al. | 128/633 |
| 4,510,938 | 4/1985 | Jobsis et al. | 128/633 |
| 4,515,165 | 5/1985 | Carroll | 128/664 |
| 4,570,638 | 2/1986 | Stoddart et al. | 128/665 |
| 4,685,464 | 8/1987 | Goldberger et al. | 128/633 |
| 4,770,179 | 9/1988 | New, Jr. et al. | 128/633 |
| 4,805,623 | 2/1989 | Jobsis | 128/633 |
| 4,819,752 | 4/1989 | Zelin | 128/633 |
| 4,825,879 | 5/1989 | Tan et al. | 128/633 |
| 4,830,014 | 5/1989 | Goodman et al. | 128/665 |
| 4,840,179 | 6/1989 | Ullrich | 128/633 |

(List continued on next page.)

FOREIGN PATENT DOCUMENTS

| | | |
|---|---|---|
| 2517129 | 6/1976 | Germany. |
| 2076963A | 12/1981 | United Kingdom. |
| WO89/09566 | 10/1989 | WIPO. |

*Primary Examiner*—Angela D. Sykes
*Attorney, Agent, or Firm*—Price, Heneveld, Cooper, DeWitt & Litton

[57] ABSTRACT

An electro-optical sensor for spectrophotometric clinical examination devices includes a thin, flexible, lightweight, elongated support frame having at least a pair of integral mounting bases. Each base is shaped and located to separately receive and position structurally independent and relatively free-standing electro-optical components including a light source and a detector. Each mounting base includes cup-like walls defining sockets of predetermined configuration of varying diameter to receive a correspondingly configured electro-optical component. An attachment device secures each component in a nested position at its respective mounting base. A plurality of discrete flexible electrical conductors extends along the support frame, each conductor being connected to a component. A shield shields at least some of the conductors from ambient sources of electrical and/or magnetic noise. A softly compliant outer cover is disposed over the support frame, components, conductors and shield. The cover has light passing portions overlying the components.

35 Claims, 3 Drawing Sheets

U.S. PATENT DOCUMENTS

| | | | |
|---|---|---|---|
| 4,865,038 | 9/1989 | Rich et al. | 128/633 |
| 4,867,557 | 9/1989 | Takatami et al. | 356/41 |
| 4,880,304 | 11/1989 | Jaeb et al. | 356/41 |
| 4,928,691 | 5/1990 | Nicholson et al. | 128/633 |
| 4,938,218 | 7/1990 | Goodman et al. | 128/666 X |
| 4,964,408 | 10/1990 | Hink et al. | 128/633 |
| 5,080,098 | 1/1992 | Willett et al. | 128/666 X |
| 5,094,240 | 3/1992 | Muz | 128/666 X |
| 5,099,842 | 3/1992 | Mannheimer et al. | 128/633 |
| 5,111,817 | 5/1992 | Clark et al. . | |
| 5,139,025 | 8/1992 | Lewis et al. | 128/665 |
| 5,140,989 | 8/1992 | Lewis et al. | 128/633 |
| 5,188,108 | 2/1993 | Secker | 128/666 X |
| 5,209,230 | 5/1993 | Swedlow et al. | 128/665 X |
| 5,217,013 | 6/1993 | Lewis et al. | 128/633 |

ELECTRO-OPTICAL SENSOR FOR SPECTROPHOTOMETRIC MEDICAL DEVICES

This is a continuation of application Ser. No. 08/065,140 filed on May 20, 1993, now abandoned.

FIELD OF THE INVENTION

This invention relates generally to the field of spectrophotometric patient-examination apparatus for clinical use on an in vivo basis, such as for example oximeters using near infrared light wavelengths to non-invasively monitor a patient to obtain the requisite data for determining blood oxygen saturation. More particularly, the invention relates to the electro-optical sensors used in such apparatus and, in particular, electro-optical sensors of this general type which are particularly useful in cerebral oximeters and which operate by compliantly conforming to the generally rounded, compound curvature of the human forehead, from where the patient data is obtained, while nonetheless maintaining essential component relative positioning.

BACKGROUND OF THE INVENTION

The use of near infrared spectrophotometry in clinical patient examination for medical purposes has grown steadily and increasingly during the last ten to twenty years, and is drawing increasing interest in more recent years, with various new developments, or proposed developments. A very commonly encountered such application is found in pulse oximeters, which have a sensor that is applied to a bodily appendage such as the ear, finger, nasal septum, etc., to detect the arterial pulse and sample data for determining the oxygen saturation of hemoglobin in the blood supply.

A more recent innovation is the cerebral oxygen saturation monitor developed by Somanetics Corporation of Troy, Mich., U.S.A., which uses sensors that are superficially similar to those used with pulse oximeters but which have distinct differences attributable to their different purpose and different point of application, i.e., the human forehead as opposed to appendages such as ears, fingers, etc., as well as to the different data-sampling and processing techniques which characterize the cerebral oximeter.

Accordingly, examples of the many different sensors intended for pulse oximeters of the type referred to above may be seen in such patents as those to Smart et at., U.S. Pat. No. 3,769,974, Kressee et at., U.S. Pat. No. 4,013,067, New et at., U.S. Pat. Nos. 4,621,643, 4,700,708, 4,770,179, Tan et at., U.S. Pat. No. 4,825,822, Goodman et at., U.S. Pat. No. 4,830,014, Rich et at., U.S. Pat. No. 4,865,038, and Muz, U.S. Pat. No. 5,094,240. There are also other examples of sensors which have certain basic similarities in overall or basic nature and function, as may be seen for example in certain of the different patents to Franz Jobsis, e.g., U.S. Pat. Nos. 4,223,680, 4,281,645, 4,321,930, 4,805,623, 4,380,240 and 4,510,938, although the actual utilization of these has apparently never taken place in any commercial apparatus, and the use and function of the related apparatus is not considered really understood; however, these patents do show electro optical components proposed for use on the human forehead, as well as other portions of the body. Apart from this, sensors which are specifically described as intended for use in cerebral oximeters have apparently only been proposed by inventors associated with Somanetics Corporation, as shown and described for example in U.S. Pat. Nos. 5,139,025 and 5,217,013, and further referred to in pending application Ser. No. 983,820 (filed Dec. 1, 1992).

While significant particular differences exist between probes used in arterial (pulse) oximeters and cerebral oximeters, and the resulting data is processed in a significantly different manner in order to arrive at the desired readout of particular physiologic parameters, the overall structural developments which have taken place in sensors for pulse oximeters is to some extent instructive and informative in connection with cerebral oximeters, even though some of the characteristic problems and considerations encountered in pulse oximeters, where the sensor is in effect wrapped around the finger or the earlobe or the bridge of the nose to position the detector substantially opposite the light source, are not encountered in cerebral oximeters. In addition, the aforementioned Somanetics Corporation cerebral oximeter characteristically uses more than one examining wavelength and both a near and far detect, which are disposed laterally from the source at particular distances which are very important to maintain. Further, while a certain amount of longitudinal flexibility is necessary for a cerebral oximeter sensor to conform to the human forehead, this is of course far less than that required to wrap around the human finger or the like, where the particular lateral distance of the detector from the source is not usually given any consideration, the principal objective being that of maintaining the fight curvature about the finger, etc. and the desired mutually opposed relationship between the electro-optical components. In a cerebral oximeter, the sensor is more nearly flat, since the degree of curvature of the human forehead is much less than that of a finger, etc., and the electro-optical components are disposed laterally adjacent rather than across from one another. Furthermore, the curvature of the forehead is typically compound in nature (i.e., both longitudinal and lateral), whereas the curvature of fingers, etc. is usually considered merely, or generally, cylindrical in nature rather than compound.

SUMMARY OF THE INVENTION

The present invention provides further significant developments in a sensor particularly adapted for cerebral oximeter applications of near infrared spectrophotometric-type apparatus and, in particular, provides a new structural concept for such sensors which may also find useful application in other such spectrophotometric-type devices. Generally speaking, this new structural concept includes a novel lightweight, thin, flexible internal support member which maintains the overall size and shape of the sensor but is readily deformable elastically for close conformance to the desired human anatomical extremity involved, e.g., the human forehead.

In particular preferred usage of the structural concept embodied by the aforementioned internal support member, it is entirely feasible to merely use in addition to such internal support member, a soft, readily deformable outer cover on the side adjacent the patient, for contact with the skin and adherence of the sensor thereto, together with a simple sheet-like rear cover or closure that provides a convenient place for printed labeling and the like and conceals the internal operating apparatus (electro-optical components, wiring, etc.) in a decorative and attractive manner. That is to say, these outer cover members need not contribute to the essential structure of the sensor, nor to the retention or positioning of the electro-optical components, or to the isolation of the latter from ambient or other light, etc.

Further, in accordance with preferred embodiments hereof, the internal frame member may define integral mounting bases for the electro-optical components, for example in the form of socket-like recesses that closely receive such components in their most preferred embodiments. Further, the novel internal support member may define integral light passages for the light emitted by the source and ultimately received by the detector after transmission through portions of the patient.

In addition, the novel sensor in accordance with the invention includes, in preferred embodiments, particular novel embodiments of the electro-optical components, in which both the sources (e.g., LEDs) and the detectors (i.e., photodiodes) are directly secured upon and electrically coupled to leadframe components, comprising conductive substrates which provide physical support as well as electrical coupling means for the light-emitting and light-receiving elements themselves. Further, these leadframe assemblies are preferably disposed within an optically transmissive material which in effect encapsulates the assembly, physically stabilizing it while simultaneously providing optimum light transmission characteristics, and in addition providing for highly desirable mounting procedures during assembly, in which the component subassembly so described in effect constitutes a small plug-like member which may be inserted into a corresponding socket-like recess integrally defined by the internal support member, whereby physical mounting is enhanced while at the same time optimal positioning is ensured.

The foregoing particular accomplishments and objectives of the invention, together with others related to or involved therein, will become increasingly clear following consideration of the ensuing detailed specification and its appended drawings, setting forth particular preferred embodiments and best modes contemplated by the inventor as of the present time. Of course, these particular preferred embodiments are to be considered as illustrative only, since modifications and variations thereof, as well as other embodiments, may be suggested thereby to those having skill in the art.

DESCRIPTION OF PREFERRED EMBODIMENTS

Figure 1:
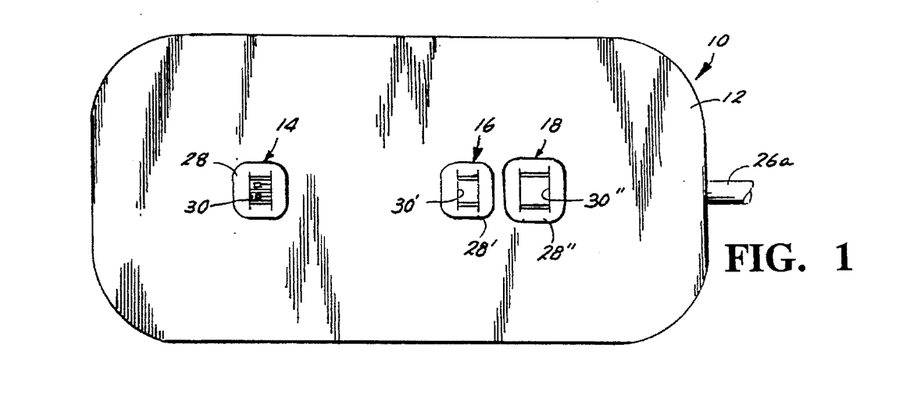
FIG. 1 is an overhead plan view of a sensor in accordance with the invention, showing basic features of the patient-contacting side.
Figure 1A:
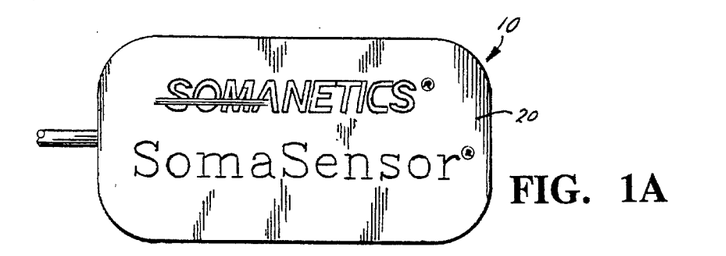
FIG. 1A is a bottom plan view of the sensor shown in FIG. 1, shown on a reduced scale.

The sensor 10 of the invention is generally illustrated in FIGS. 1 and 1A, and basically includes an outer portion defined by a cover 12 of soft, compliant material disposed on the side facing the patient during use, through which are exposed (e.g., through apertures in the cover) certain electro-optical components including a light source 14 and a pair of receivers 16, 18, each of which are located at particular distances from source 14 (as more particularly described in co-pending applications Ser. Nos. 329,945 and 711,452, which are incorporated herein by reference). The soft, compliant nature of cover 12 is principally dictated by considerations of patient comfort, although it is preferably used as part of the means for mounting the sensor upon the forehead of the patient in self-retaining relation; i.e., the outer surface of cover 12 preferably carries a coating of adhesive over its entire surface (for example, the 3-M transfer adhesive identified as #1524), covered by a readily removable outer liner (not shown) until used. As noted in the referenced co-pending applications, the cover component may advantageously consist of the commercially available material known as "Poron", which is an open-celled (moisture-transmissible) polymeric foam. The rear cover 20 of the sensor 10 may simply consist of a continuous sheet of flexible, thin sheet material which conceals the interior components and structure. This layer need not be a soft, compliant foam, and may simply conceal the internal components, provide a finished outer appearance, and preferably be of a nature as to carry the manufacturers' names and/or marks, as illustrated in FIG. 1A, together with comments or instructions as to use; however, it is desirable that it also be moisture transmissive, so that it and the front cover 12 may cooperate to dissipate moisture.

Figure 2:
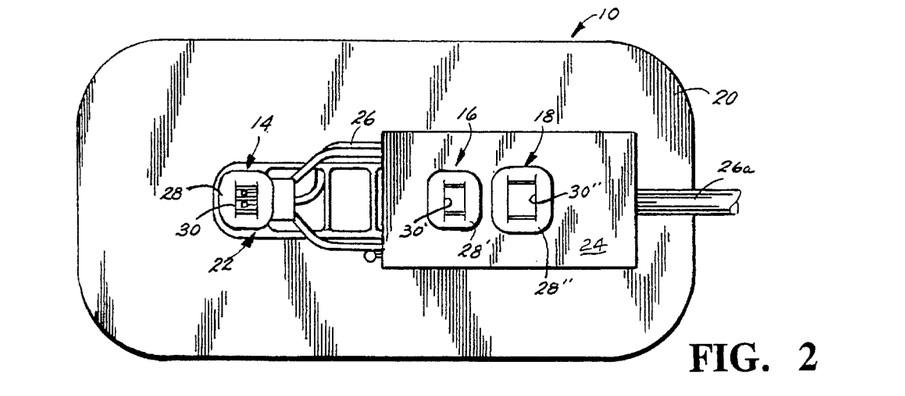
FIG. 2 is a top plan view of the sensor shown in the previous figures with the outer cover removed to show certain internal structure.

As shown in FIG. 2, the sensor 10 has its front cover 12 removed to show certain internal components. These include the support frame 22 referred to in substantial detail hereinafter, together with one of the shield members 24, and certain of the electrical conductors 26, which are connected to the source 14 and detectors 16, 18 to provide excitation and/or couple signals back to the oximeter unit. Preferably, in accordance with the invention, the conductors 26 are comprised of independent wires of a standard nature, each carrying its own insulation and enclosed with the others in a cable 26a that preferably includes an outer coaxial sheath to help provide a low-noise operating environment, such sheath being in effect another shield that is coupled to the shield 24 and its counterpart, described hereinafter. As may be seen in FIG. 2, the support frame 22 defines integral hub-like bosses 28, 28', 28", in which apertures 30, 30', 30" are formed to provide light-transfer passages for the electro-optical components 14, 16, 18.

Figure 3:
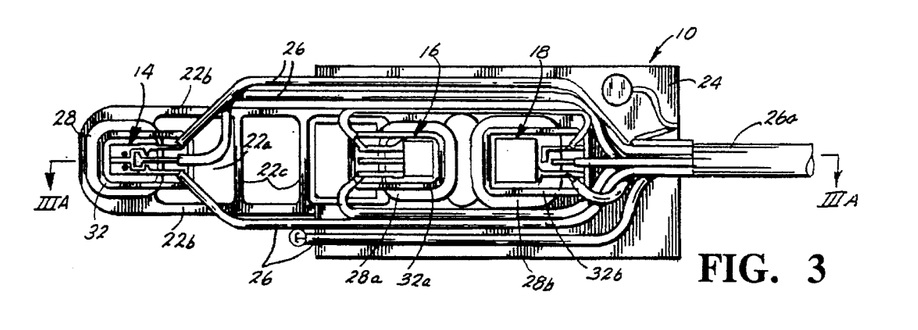
FIG. 3 is a bottom plan view of the sensor with both covers off, showing further internal details.
Figure 3A:
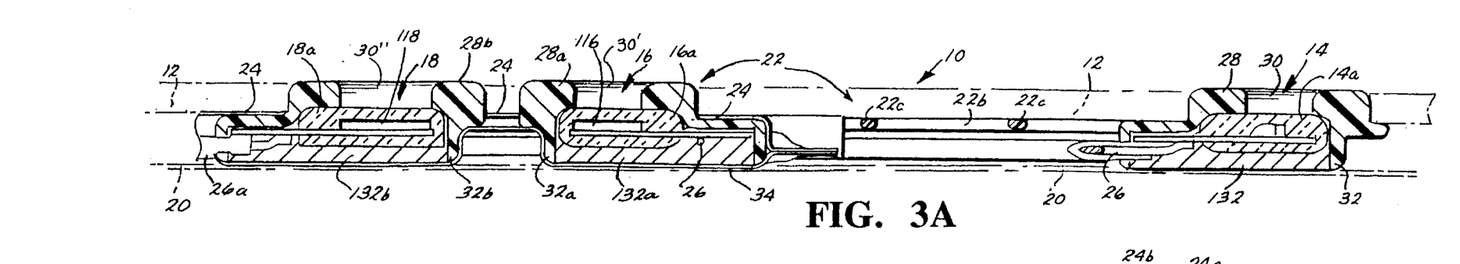
FIG. 3A is an enlarged, longitudinal sectional elevation taken along the plane A—A of FIG. 3, with certain structure removed for clarity, showing further structural details.
Figure 4:
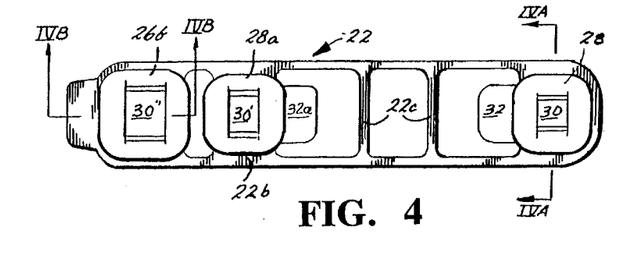
FIG. 4 is an overhead plan view of the internal support frame used in the sensor.
Figure 4A:
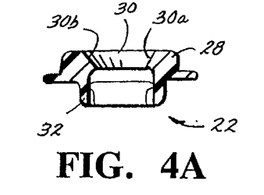
FIG. 4A is a transverse cross-sectional view taken along the plane A—A of FIG. 4.
Figure 4B:
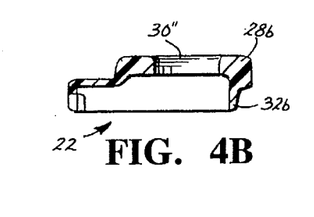
FIG. 4B is a longitudinal sectional view taken along the plane B—B of FIG. 4.
Figure 5:
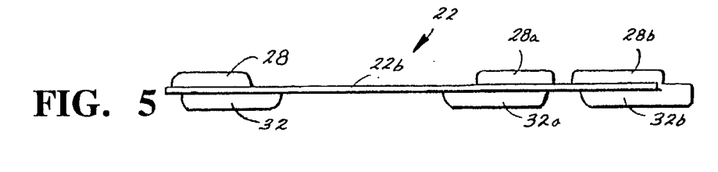
FIG. 5 is a side elevational view of the structure shown in FIG. 4.

Further details as to the internal structure of the sensor 10 may be seen in FIGS. 3 and 3A, in which both the front and rear covers 12, 20 are removed, but have their positions shown in phantom. FIG. 3 shows the sensor 10 from the rear side, and further illustrates the overall shape of the support frame 22 as being an elongated lattice-like member that preferably includes a plurality of openings 22a defined by longitudinally-extending side portions 22b and cross members 22c. As may also be seen in FIG. 3, the support frame 22 preferably defines integral socket like recesses 32, 32a, 32b, which receive and mount the electro-optical components comprising source 14 and detectors 16 and 18. In addition, the lowermost portions of the aforementioned bosses 28, 28a, 28b may be seen in FIG. 3.

FIG. 3A, as well as FIGS. 4, 4A, 4B, and 5 all serve to better illustrate the support frame 22 and the integral structures which it defines, i.e., the bosses 28, socket-like recesses 32, light-passage apertures 30, etc. In this regard, it will be noted that the two oppositely-disposed sides 30a, 30b of each of the apertures 30, 30', 30" are preferably angled at approximately 45° to provide a frusto-conical shape that better achieves both outward light emission from source 14 and inward light-gathering by the detectors 16 and 18. The other two sides of the apertures 30 are parallel to better optically define the electro-optical component separation distances. The entire support frame 22 is preferably an integral structure, formed as one piece by injection molding or the like, and is in the preferred embodiment a readily flexible member which possesses sufficient structural rigidity to be self-shape-retaining; e.g., the frame 12 may be sufficiently flexible as to self-deflect (i.e., droop) slightly when held cantilevered by one end, with the remainder projecting, but is preferably not so flexible as to sag substantially, e.g., into a vertical disposition, under such circumstances. While various polymerits will provide such a structure, a preferred one is the industrial plastic known by the trademark "Delrin," which, as preferred, is available in a black color which is opaque to both ambient light and the particular light spectra emitted by the source 14, as well as being electrically insulating in nature. In the preferred lattice-like, openwork structure, the frame 22 has minimal mass and thickness, but nonetheless embodies all of the desired characteristics of flexibility, shape-retention, etc., notwithstanding its exceedingly thin dimension. In this regard, it should be noted that the cross members 22c maintain the position of the longitudinal members 22b, preventing bowing of the latter, etc. and thus help to particularly maintain the relative spacing of the light passages 30, 30', and 30", which is of significant importance to the operation of the preferred cerebral oximeter (as noted, for example, in the referenced co-pending application Ser. No. 329,945).

Figure 7:
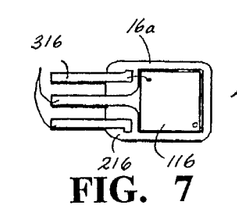
FIG. 7 is a plan view showing a preferred embodiment of one of the detector electro-optical component subassemblies.
Figure 8:
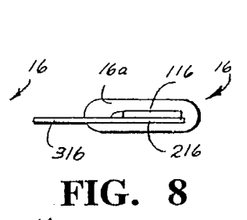
FIG. 8 is a side elevational view of the structure shown in FIG. 7.
Figure 9:
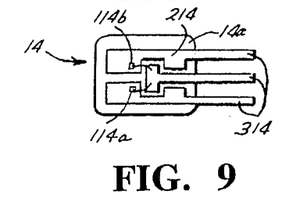
FIG. 9 is a plan view showing a preferred embodiment of the emitter electro-optical component subassembly.
Figure 10:
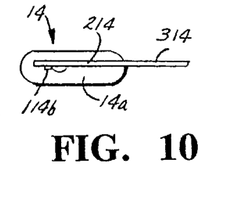
FIG. 10 is a side elevational view of the structure shown in FIG. 9.

As further illustrated in FIG. 3A, the socket-like recesses 32, 32a and 32b are integrally associated with the light-passage apertures 30, 30', 30" and provide a self-indexing seat or base for the electro-optical components 14, 16, 18. More particularly, each of the electro-optical components, generally designated 14, 16 and 18, preferably comprises an assembly, as may be seen in FIG. 3A and as illustrated in further detail in FIGS. 7 and 8 (showing detector 16, as representative of either such detector) and FIGS. 9 and 10, showing source 14. With reference to FIGS. 7 and 8, the detector component 16 comprises a solid state photodiode 116 secured directly atop a supportive leadframe assembly 216 having a plurality of outwardly projecting terminals 316 by which it may be connected to operating excitation and by which its output may be coupled to the processor in the oximeter or other such device. As is known, leadframe components such as that shown at 216 comprise a thin but generally rigid conductive metal substrate, which in accordance with a preferred implementation is silver plated. The photodiode 116 is secured to leadframe 216 by electrically conductive epoxy (preferably, silver-filled epoxy) and electrically connected to the leadframe by wire-bonding, preferably using gold wire to complete the circuit. An important further preferred feature of all of the electro-optical components or subassemblies, referred to in further detail hereinafter, is the presence of an eneapsulating deposit 16a of optically dear material such as the epoxy known as Hysol, type MG18, available from The Dexter Corporation of Industry, CA., which completely covers the active electro-optic dement and portions of the leadframe. As explained further brow, the outer size and shape of this deposit preferably has particular attributes.

With reference to FIGS. 9 and 10, showing the source electro-optical component 14, a structure directly analogous to that shown in FIGS. 7 and 8 and described above is involved, with directly analogous numbering being used; however, it will be noted that this component preferably includes a pair of LEDs, designated 114a, 114b. As in the case of the photodiode detector 116, the LEDs 114a, 114b are secured to their leadframe 214 by electrically conductive silver epoxy and wire-bonded thereto to complete the circuit. With respect to both such types of component subassembly, it is to be particularly noted that the leadframes 214, 216 should preferably be as large as the sensor configuration will permit, to provide the maximum possible heat-sinking and light-reflection.

Referring now again to FIG. 3A, it may be appreciated that the outer size and shape of the optically clear enclosing deposits 14a, 16a, 18a is preferably made to be directly complementary to the shape of its corresponding socket-like recess 32, 32a, 32b, formed by the frame 22, so that each such electro-optical component may be inserted into its corresponding socket in relatively close-fitting relation. By so doing, each such electro-optical component is in effect automatically indexed into its proper position during assembly without the requirement of any fixturing, etc. such as otherwise would be essential in order to assure the proper positioning, and relative positioning, of each of these operating components. Thus, not only is proper positioning automatically attained for each of the LEDs and detectors relative to their corresponding apertures 30, 30', 30", for optimum optical performance relative to the patient, but in addition the particular desired lateral distance between the source 14 and the two different detectors 16, 18 is automatically insured. Furthermore, the structure just described positions the electro-optical components close to the adjacent periphery of the patient in actual use (i.e., the flat outer face of each boss 28) and, of considerable importance, each active electro optical element is automatically and repeatably positioned in essentially the same location in each different sensor, such that the operating results of each sensor will be essentially uniform and the accuracy and consistency of the corresponding oximeter or other such clinical device will be significantly augmented. That is, with the preferred construction and structure, each of the LEDs and detectors in each sensor is disposed in essentially the same plane and not only has consistent and close positioning relative to the patient but in addition has essentially the same angular disposition with respect to the other such operative components, and from one sensor to the next.

As further illustrated in FIG. 3A, each of the electro-optical component subassemblies 14, 16, 18 is secured in place within its respective recess 32, 32a, 32b by a deposit of epoxy or other such potting compound 132, 132a, and 132b which essentially fills the outer portion of each such recess. It is important that this material be opaque to both ambient and operating light spectra, and also that the frame 22 itself, including its integral bosses 28, 28a, 28b and socket-like recess projections 32, 32a, 32b have this characteristic. Also, both the bosses 28 (and entire frame 22) and compound 132 are preferably moisture-impermeable. Accordingly, each of the electro-optical component subassemblies is in effect sealed within its own opaque chamber, whose only path for light passage is the apertures 30, 30', 30". Since the sensor is configured so that the flat upper face of each of the bosses 28, 28a, 28b will lie flush against the skin of the patient, with the frame 22 and its overlying substrates flexing to conform to the particular physiologic conformation of each patient, the outer end of each such light aperture/passage is in effect sealed to the patient and defines a basically closed passage in which the only light which may reach the detectors 16, 18 is that which has been emitted by the source 14 and has passed through adjacent portions of the patient by transmissivity. It will be appreciated that the aforementioned adhesive layer on the outside of front cover 12 will, by its direct contact with the forehead of the patient, serve to hold the flat upper face of each of the bosses 28 in close contact with the skin of the patient. In this regard, the thickness of the front cover 12 is (as indicated in FIG. 3A) preferably slightly less than the amount by which the bosses 28 protrude beyond the rest of the frame 22, since this will help maintain continuing tight contact between the outer faces of the bosses and the skin of the patient. Of course, like the front shield 24, front cover 12 has apertures extending through it which are carefully sized, shaped and located so as to fit closely over the projecting bosses 28.

Figure 11:
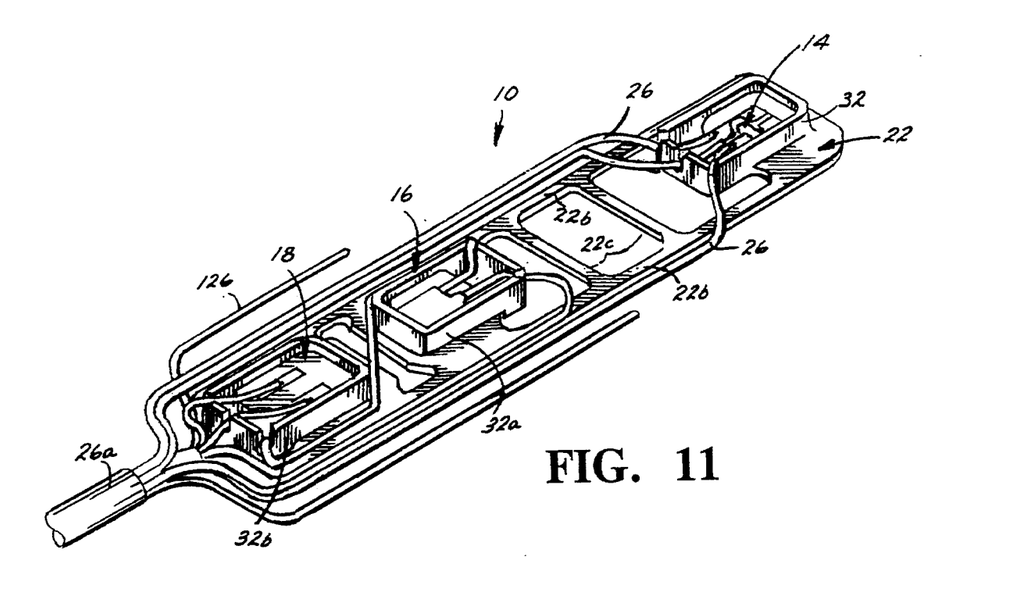
FIG. 11 is a perspective view showing the bottom of the support frame and illustrating a first point during assembly of the sensor.
Figure 12:
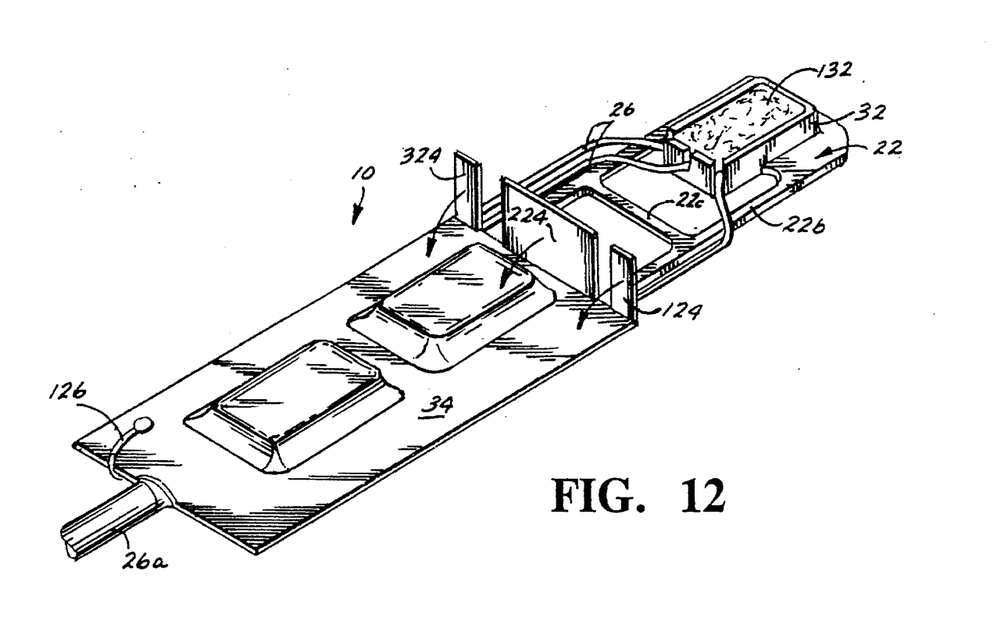
FIG. 12 is a perspective view of the structure shown in FIG. 11 together with additional elements, illustrating another point during assembly.

The manner in which the sockets or recesses 32 are filled with the sealing epoxy or other such potting compound 132 is further illustrated in FIG. 12, which with FIG. 11 shows the sensor 10 during different phases of assembly, with the frame 22 shown in an inverted position in which the sockets 32, 32a, 32b open upwardly for receipt of the corresponding electro-optical components, already secured to electrical cable 26a and its individual different conductors 26 (as shown in FIG. 11). In this regard, it will be noted that the edge of each of the sockets 32 is preferably slotted in a manner to individually route and frictionally retain the related conductors 26.

Figure 6:
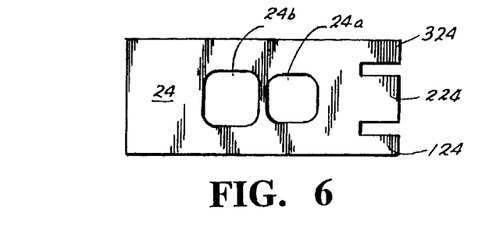
FIG. 6 is an overhead plan view of one of the shield members used in the sensor.

After such poring or sealing of the electro-optical components within their corresponding sockets 32, the assembly is largely completed, but the aforementioned front and rear shields 24, 34 are then laid in place and secured to one another. More particularly, the front shield 24 is illustrated in more detail in FIG. 6, from which it may be seen that the same includes a pair of apertures 24a, 24b which are sized to closely fit over the projecting bosses 28a, 28b, respectively, in the support frame (FIG. 3A). As further seen in FIG. 6, the shield 24 is preferably notched on one end to provide projecting tabs 124, 224, 324. The purpose of these tabs may readily be seen in FIG. 12, i.e., the same are bent laterally and folded over upon the rear shield 34, as shown by the arrows. This is accomplished by folding each of the side projections or tabs 124, 324 back along the outer edges of the frame 22, and folding the center tab 224 through a correspondingly located opening in frame 22, between a pair of the cross members 22b. Apart from the projecting tabs just noted, both shields 24 and 34 are of the same size and basic shape, and both are preferably made of thin copper sheet, in particular copper tape having its own layer of electrically conductive adhesive (for example, 3M no. 1181) by which the shields are secured to adjacent portions of frame 22 as well as to one another, around their corresponding overlapped edges (FIG. 12).

As further seen in FIG. 12, the rear shield 34 (which is simply rectangular in shape) is preferably deformed during assembly to lie closely about the sockets 32a and 32b of frame 22 which hold detectors 16 and 18, respectively, so that each of the two shield members sheets 24–34 is in very close, intimate contact with its corresponding portion of the sensor 10, to present a thin and substantially flat overall package. Of course, folding the tabs 124, 224 and 324 over and against the rear surface of shield 34 places both shields in direct contact with one another, but their mutual electrical contact is preferably assured by soldering tab 224 to the rear surface of shield 34. Furthermore, the aforementioned coaxial sheath in cable 26a, which forms an additional shield portion, is preferably coupled by a short electrical lead 126 to the rear of shield member 34, where it is preferably soldered in place. Thus, the entire detector area of the sensor 10 is very thoroughly and closely shielded from ambient sources of electrical noise, such as stray RF fields, etc., except for only the immediate area in front of the source and detectors, and it should be understood that such extensive shielding is important in a device of this nature, particularly in view of applications such as the aforementioned cerebral oximeter, in which the amount of light remaining after transmission through the adjacent skin, skull, and brain extremities represents an extremely small quantity, essentially measured in photons, with corresponding signal levels from the detectors being extremely small. Thus, it will be appreciated that the tolerable noise level is extremely small, and the more that this can be reduced, the more accuracy the system will have.

With further reference to the electro-optical components 14, 16 and 18, and to their operation in conjunction with the integral light-passage ports or windows 30, 30', and 30" provided by frame 22, it is to be noted that the preferred structural arrangement described serves to position each of the active electro-optical elements (LEDs and photodiodes) directly centered of its corresponding light passage 30, 30' and 30". In addition, each of these passages has a cross-sectional shape which directly complements that of its corresponding electro-optical component, i.e., essentially square, or rectangular. Furthermore, the cross-sectional area of the light passages 30' and 30" for the respective detectors or sensors 16 and 18, corresponds reasonably closely to the size of the electro-optical component involved, for enhanced optical coupling and performance consistency. These achievements are augmented by the fact that the thickened structure defining the bosses 28, 28a, and 28b renders them essentially non-flexible under normal operating circumstances, notwithstanding the overall flexibility of the frame 22, covers 12, 20, shields 24, 34, and sensor 10 generally, with respect to conforming to individual patient forehead configurations. Further, the aforementioned angularly-shaped edges or walls 30a, or 30b (FIG. 4A) on the two lateral sides of each light passage help augment both light emission from the source and light reception by the detectors; on the other hand, the essentially vertical other two walls of each such light passage (relative to the longitudinal axis of the sensor 10) augment the effective retention of the particular spacing between the electro-optical components, whose importance is referred to above. A final aspect of the electro-optical components is the preferred use of a larger photodiode as the "far" detector in 18, in view of its greater distance from source 14 and corresponding lower likelihood of substantial photon reception at that point. More particularly, the near detector 116 may be implemented by use of a 7.6 square millimeter photodiode, while the far detector 18 is preferably twice that large, i.e., 15 square millimeters.

It is to be understood that the above detailed description is that of one exemplary preferred embodiment of the invention, and that numerous changes, alternations and variations may be made without departing from the underlying concepts and broader aspects of the invention as set forth in the appended claims, which are to be interpreted in accordance with the established principles of patent law, including the doctrine of equivalents.

The embodiments of the invention in which an exclusive property or privilege is claimed are defined as follows.

1. An electro-optical sensor for spectrophotometric-type clinical examination devices, comprising in combination: a thin, flexible, lightweight, elongated support frame having at least a pair of integral mounting bases, each particularly shaped and located to separately receive, support and position a particular one of at least a pair of structurally independent and mutually free-standing electro-optical components including a light source and detector, each of said integral mounting bases including cup-like walls defining sockets of predetermined configuration of varying diameter to nestingly receive its correspondingly configured electro-optical component; an attachment device securing each such component in its nested position at its respective one of said mounting bases; a plurality of discrete flexible electrical conductors extending along said support frame, each such conductor being connected to at least one of said components to electrically enable the same for operation; a shield for shielding at least some of said conductors connected to said detector from ambient sources of electrical and/or magnetic noise; and a softly compliant outer cover disposed over said support frame, said mounted components, conductors and shield, said cover having light-passing portions overlying said components for passage of light from said source outwardly of said sensor and reception of resulting light from beyond said sensor by said detector; said support frame and combined elements providing the structural support to hold and maintain said electro-optical components in predetermined particular relative locations and orientations during use of said sensor in said clinical examinations.

2. An electro-optical sensor according to claim 1, wherein said support frame is comprised of material which is substantially opaque to the light emitted by said source.

3. An electro-optical sensor according to claim 1, wherein said support frame is comprised of electrically insulative material.

4. An electro-optical sensor according to claim 1, wherein said support frame is comprised of material which is substantially opaque to the light emitted by said source and also to ambient light, thus optically isolating the electro-optical components from each other and from ambient light.

5. An electro-optical sensor according to claim 1, wherein said support frame includes means defining integral light passages disposed directly adjacent and in alignment with at least said detector.

6. An electro-optical sensor according to claim 1, wherein said support frame has sufficient bending strength to be self-shape-retaining in the absence of external distorting forces but also has sufficient flexibility to elastically deflect laterally under light manual forces.

7. An electro-optical sensor for spectrophotometric-type clinical examination devices, comprising in combination: a thin, flexible, lightweight, elongated support frame having at least a pair of integral mounting bases, each particularly shaped to separately receive and position a particular one of at least a pair of electro-optical components including a light source and detector in a particular relative location and orientation, each of said integral mounting bases including cup-like generally annular walls of varying cross-section for nestingly receiving a correspond electro-optical component; apparatus securing each such component in its nested position at its respective one of said mounting bases; a plurality of discrete flexible electrical conductors extending along said support frame, each such conductor being connected to at least one of said components to electrically enable the same for operation; a shield for shielding at least some of said conductors connected to said detector from ambient sources of electrical and/or magnetic noise; and a softly compliant outer cover disposed over said support frame, said mounted components, conductors and shield, said cover having light-passing portions overlying said components for passage of light from said source outwardly of said sensor and reception of resulting light from beyond said sensor by said detector, said support frame including means defining integral light passages disposed directly adjacent and in alignment with at least said detector, at least one of said light passages including peripheral walls which extend angularly and divergently outward from said detector to their opposite end extremity.

8. An electro-optical sensor according to claim 7, wherein said light passages include peripheral walls which are defined by and integrally formed with said support frame.

9. An electro-optical sensor for spectrophotometric-type clinical examination devices, comprising in combination: a thin, flexible, lightweight, elongated support frame having at least a pair of integral mounting bases, each particularly shaped to separately receive and position a particular one of at least a pair of electro-optical components including a light source and detector in a particular relative location and orientation, each of said integral mounting bases including cup-like generally annular walls of varying cross-section for nestingly receiving a corresponding electro-optical component; apparatus securing each such component in its nested position at its respective one of said mounting bases; a plurality of discrete flexible electrical conductors extending along said support frame, each such conductor being connected at least to at least one of said components to electrically enable the same for operation; a shield for shielding at least some of said conductors connected to said detector from ambient sources of electrical and/or magnetic noise; and a softly compliant outer cover disposed over said support frame, said mounted components, conductors and shield said cover having light-passing portions overlying .said components for passage of light from said source outwardly of said sensor and reception of resulting light from beyond said sensor by said detector, said frame having a thickness which is on the order of about only three to ten times the thickness of said electro-optical components.

10. An electro-optical sensor according to claim 9, wherein said frame defines integrally formed socket-like recesses for receiving and positioning said electro-optical components, said recesses including said cup-like generally annular walls.

11. An electro-optical sensor according to claim 10, wherein said support frame includes means defining integral light passages disposed directly adjacent and in alignment with at least said detector.

12. An electro-optical sensor for spectrophotometric-type clinical examination devices, comprising in combination: a thin, flexible, lightweight, elongated support frame having at least a pair of integral mounting bases, each particularly shaped to separately receive and position a particular one of at least a pair of electro-optical components including a light source and detector in a particular relative location and orientation, each of said integral mounting bases including cup-like generally annular walls of varying cross-section for nestingly receiving a corresponding electro-optical component; apparatus securing each such component in its nested position at its respective one of said mounting bases; a plurality of discrete flexible electrical conductors extending along said support frame, each such conductor being connected to at least one of said components to electrically enable the dame for operation; a shield for shielding at least some of said conductors connected to said detector from ambient sources of electrical and/or magnetic noise; and a softly compliant outer cover disposed over said support frame, said mounted components, conductors and shield, said cover having light-passing portions overlying said components for passage of light from said source outwardly of said sensor and reception of resulting light from beyond said sensor by said detector, said support frame defining integrally formed socket-like recesses for receiving and positioning said electro-optical components, said recesses including said cup-like generally annular walls, said frame including means defining integral light passages disposed directly adjacent and in alignment with at least said detector, and said frame having oppositely-disposed sides and said socket-like recesses opening outwardly from said frame on a first of said sides while said light passages open outwardly of the other such side, for access to said socket-like recesses from said first side.

13. An electro-optical sensor according to claim 12, wherein said light passages include peripheral walls which are defined by and integrally formed with said support frame.

14. An electro-optical sensor according to claim 13, wherein the overall thickness of said frame at the location of said passages and recesses is only on the order of about six to ten times the thickness of said detector component.

15. An electro-optical sensor according to claim 12, and further including means substantially filling said socket-like recesses from said first side to seal said components in their respective such recesses.

16. An electro-optical sensor according to claim 15, wherein said filling means comprises a material generally opaque to at least ambient light.

17. An electro-optical sensor for spectrophotometric-type clinical examination devices, comprising in combination: a thin, flexible, lightweight, elongated support frame having at least a pair of integral mounting bases, each particularly shaped to separately receive and position a particular one of at least a pair of electro-optical components including a light source and detector in a particular relative location and orientation, each of said integral mounting bases including cup-like generally annular walls of varying cross-section for nestingly receiving a corresponding electro-optical component; apparatus securing each such component in its nested position at its respective one of said mounting bases; a plurality of discrete flexible electrical conductors extending along said support frame, each such conductor being connected to at least one of said components to electrically enable the same for operation; a shield for shielding at least some of said conductors connected to said detector from ambient sources of electrical and/or magnetic noise; and a softly compliant outer cover disposed over said support frame, said mounted components, conductors and shield, said cover having light-passing portions overlying said components for passage of light from said source outwardly of said sensor and reception of resulting light from beyond said sensor by said detector said support frame comprising an openwork member having longitudinally extending side portions and cross-members interconnecting said side portions to resist bowing thereof.

18. An electro-optical sensor according to claim 17, wherein said support frame comprises a molded elastomeric member.

19. An electro-optical sensor for spectrophotometric-type clinical examination devices, comprising in combination: a thin, flexible, lightweight, elongated support frame having at least a pair of integral mounting bases, each particularly shaped to separately receive and position a particular one of at least a pair of electro-optical components including a fight source and detector in a particular relative location and orientation, each of said integral mounting bases including cup-like generally annular walls of varying cross-section for nestingly receiving a corresponding electro-optical component; apparatus securing each such component in its nested position at its respective one of said mounting bases; a plurality of discrete flexible electrical conductors extending along said support frame, each such conductor being connected to at least one of said components to electrically enable the same for operation; a shield for shielding at least some of said conductors connected to said detector from ambient sources of electrical and/or magnetic noise; and a softly compliant outer cover disposed over said support frame, said mounted components, conductors and shield, said cover having light-passing portions overlying said components for passage of light from said source outwardly of said sensor and reception of resulting light from beyond said sensor by said detector, said support frame defining integrally formed socket-like recesses for receiving and positioning said electro-optical components, said recesses including said cup-like generally annular walls, said electro-optical components including electrically actuated light-responsive elements disposed within optically transmissive bodies, said bodies having a size and shape generally complementary to and receivable within said socket-like recesses and against said cup-like generally annular walls.

20. An electro-optical sensor according to claim 19, and further including means retaining said optically transmissive component bodies within their respective recesses.

21. An electro-optical sensor according to claim 20, wherein said retaining means comprises at least in part peripheral portions of said socket-like recesses defining said cup-like generally annular walls.

22. An electro-optical sensor according to claim 21, wherein said retaining means further comprises an adhesive.

23. An electro-optical sensor according to claim 19, and further including means substantially filling portions of said socket-like recesses not occupied by said optically transmissive component bodies to seal said components in their respective such recesses.

24. An electro-optical sensor according to claim 23, wherein said filling means comprises a material generally opaque to at least ambient light.

25. An electro-optical sensor for spectrophotometric-type clinical examination devices, comprising in combination: a thin, flexible, lightweight, elongated support frame having at least a pair of integral mounting bases, each particularly shaped to separately receive and position a particular one of at least a pair of electro-optical components including a light source and detector in a particular relative location and orientation, each of said integral mounting bases including cup-like generally annular walls of varying cross-section for nestingly receiving a corresponding electro-optical component; apparatus securing each such component in its nested position at its respective one of said mounting bases; a plurality of discrete flexible electrical conductors extending along said support frame, each such conductor being connected to at least one of said components to electrically enable the same for operation; a shield for shielding at least some of said conductors connected to said detector from ambient sources of electrical and/or magnetic noise; and a softly compliant outer cover disposed over said support frame, said mounted components, conductors and shield, said cover having light-passing portions overlying said components for passage, of light from said source outwardly of said sensor and reception of resulting light from beyond said senior by said detector, said electro-optical components each including at least one electrically actuated light-responsive element mounted physically on and electrically coupled to a thin conductive lead frame member, said flexible electrical conductors being connected to said lead frame members.

26. An electro-optical sensor according to claim 25, wherein at least portions of said lead frame members and their attached light-responsive elements are disposed within optically transmissive bodies as an integral structure.

27. An electro-optical sensor for spectrophotometric-type clinical examination devices, comprising in combination: a thin, flexible, lightweight, elongated support frame having at least a pair of integral mounting bases, each particularly shaped to separately receive and position a particular one of at least a pair of electro-optical components including a light source and detector in a particular relative location and orientation, each of said integral mounting bases including cup-like generally annular walls of varying cross-section for nestingly receiving a corresponding electro-optical component; apparatus securing each such component in its nested position at its respective one of said mounting bases; a plurality of discrete flexible electrical conductors extending along said support frame, each such conductor being connected to at least one of said components to electrically enable the same for operation; a shield for shielding at least some of said conductors connected to said detector from ambient sources of electrical and/or magnetic noise; and a softly compliant outer cover disposed over said support frame, said mounted components, conductors and shield, said cover having light-passing portions overlying said components for passage of light from said source outwardly of said sensor and reception of resulting light from beyond said sensor by said detector, said socket-like recesses terminating in outer extremities and said shield including a sheet-like member which overlies at least certain of said socket-like recesses receiving said electro-optical components and is conformably configured to the said outer extremities of said recesses.

28. An electro-optical sensor according to claim 27, wherein said socket-like recesses open outwardly from said frame on a first side thereof disposed opposite said light passages, for access to said recesses from said first side, said sheet-like shielding member overlying and covering said recesses and the electro-optical components disposed therein.

29. In an electro-optical sensor for spectrophotometric-type equipment used in clinical patient examination and having electro-optical components including at least an optical source and detector, the improvement comprising a thin, generally flat, light-weight, longitudinally flexible support member for receiving and mounting said components in predetermined relative positions, said support member comprising a one piece molded structure of openwork configuration, said support member including means defining integral light passages disposed directly adjacent and in alignment with at least said detector.

30. In an electro-optical sensor for spectrophotometric-type equipment used in clinical patient examination and having electro-optical components including at least an optical source and detector, the improvement comprising a thin, generally flat, light-weight, longitudinally flexible support member for receiving and mounting said components in predetermined relative positions, said support member comprising a one piece molded structure of openwork configuration, said support member including means defining integral light passages disposed directly adjacent and in alignment with at least said detector, and said light passages including peripheral walls having at least portions which extend angularly and divergently outward from said detector.

31. The improvement according to claim 30, wherein said frame defines integrally formed socket-like recesses for receiving and positioning said electro-optical components.

32. In an electro-optical sensor for strophiometric-type equipment used in clinical patient examination and having electro-optical components including at least an optical source and detector, the improvement comprising a thin, generally flat, light-weight, longitudinally flexible support member for receiving and mounting said components in predetermined relative positions, said support member comprising a one piece molded structure of openwork configuration, said frame defining integrally formed socket-like recesses for receiving and positioning said electro-optical components, said support frame including means defining integral light passages disposed directly adjacent and in alignment with at least said detector, said socket-like recesses opening outwardly from said frame on a side thereof disposed opposite said light passages, for access to said recesses from said opposite side.

33. The improvement according to claim 32, wherein the overall thickness of said frame at the location of said passages and recesses is only on the order of about six to ten times the thickness of said detector component.

34. The improvement according to claim 32, wherein said support frame has sufficient bending strength to be self-shape-retaining in the absence of external distorting forces but also has sufficient flexibility to elastically deflect laterally under light manual forces.

35. In an electro-optical sensor for spectrophotometric-type equipment used in clinical patient examination and having electro-optical components including at least an optical source and detector, the improvement wherein said electro-optical components include electrically actuated light-responsive elements disposed within optically transmissive bodies, and wherein said bodies are of a size and shape generally complementary to and receivable in nested relationship within cup-like mounting recesses provided by said sensor, said electro-optical components each including at least one electrically actuated light-responsive element mounted physically on and electrically coupled to a thin conductive lead frame member, said optically transmissive bodies being disposed upon at least portions of said lead frame members.

* * * * *

UNITED STATES PATENT AND TRADEMARK OFFICE
CERTIFICATE OF CORRECTION

PATENT NO. : 5,465,714
DATED : November 14, 1995
INVENTOR(S) : Richard S. Scheuing It is certified that error appears in the above-indentified patent and that said Letters Patent is hereby corrected as shown below:

Column 1, line 47

"et at" should be --et al--.

Column 1, line 48

"et at" should be --et al--.

Column 1, line 49

"et at" should be --et al--.

Column 1, lines 49 & 50

"et at" should be --et al--.

Column 1, line 50

"et at" should be --et al--.

UNITED STATES PATENT AND TRADEMARK OFFICE
CERTIFICATE OF CORRECTION

PATENT NO.  : 5,465,714
DATED       : November 14, 1995
INVENTOR(S) : Richard S. Scheuing It is certified that error appears in the above-indentified patent and that said Letters Patent is hereby corrected as shown below:

Column 1, line 50 (2nd occurrence)

"et at" should be --et al--.

Column 2, line 17

"detect" should be --detector--.

Column 2, line 26

"fight" should be --tight--.

Column 6, line 14

"dear" should be --clear--.

Column 6, line 18

"dement" should be --element--.

UNITED STATES PATENT AND TRADEMARK OFFICE
CERTIFICATE OF CORRECTION

PATENT NO. : 5,465,714

DATED : November 14, 1995

INVENTOR(S) : Richard S. Scheuing

It is certified that error appears in the above-indentified patent and that said Letters Patent is hereby corrected as shown below:

Column 6, line 19

"brow" should be --below--.

Column 7, line 50

"poring" should be --potting--.

Column 10, Claim 7, line 9

"correspond" should be --corresponding--.

UNITED STATES PATENT AND TRADEMARK OFFICE
CERTIFICATE OF CORRECTION

PATENT NO. : 5,465,714
DATED : November 14. 1995
INVENTOR(S) : Richard S. Scheuing It is certified that error appears in the above-indentified patent and that said Letters Patent is hereby corrected as shown below:

Column 11, Claim 12, line 15

"dame" should be --same--.

Column 12, Claim 19, line 17

"fight" should be --light--.

Column 14, Claim 32, line 25

"strophiometric" should be --spectrophotometric--.

Signed and Sealed this

Twenty-fifth Day of June, 1996

Attest:

BRUCE LEHMAN

*Attesting Officer*  *Commissioner of Patents and Trademarks*